United States Patent
Hamdi et al.

(10) Patent No.: US 9,609,875 B2
(45) Date of Patent: Apr. 4, 2017

(54) METHODS FOR THE PREVENTION AND CONTROL OF PATHOGENIC INFECTIONS IN BEES AND RELATIVE COMPOSITION

(75) Inventors: Chadlia Hamdi, Etthadhamen, TN (US); Daniele Daffonchio, Milan (IT)

(73) Assignee: UNIVERSITA' DEGLI STUDI DI MILANO, Milan (IT)

( * ) Notice: Subject to any disclaimer, the term of this patent is extended or adjusted under 35 U.S.C. 154(b) by 0 days.

(21) Appl. No.: 13/695,479

(22) PCT Filed: May 3, 2011

(86) PCT No.: PCT/EP2011/057029
§ 371 (c)(1),
(2), (4) Date: Nov. 30, 2012

(87) PCT Pub. No.: WO2011/138310
PCT Pub. Date: Nov. 10, 2011

(65) Prior Publication Data
US 2013/0064796 A1    Mar. 14, 2013

(30) Foreign Application Priority Data

May 4, 2010   (IT) .............................. MI2010A0776

(51) Int. Cl.
| | |
|---|---|
| *C12N 1/20* | (2006.01) |
| *A61K 35/74* | (2015.01) |
| *A61P 31/04* | (2006.01) |
| *A01N 63/02* | (2006.01) |
| *A01K 51/00* | (2006.01) |
| *A01N 63/00* | (2006.01) |

(52) U.S. Cl.
CPC .............. *A01N 63/02* (2013.01); *A01K 51/00* (2013.01); *A01N 63/00* (2013.01)

(58) Field of Classification Search
CPC ......... A01N 63/02; A01N 63/00; A01K 51/00
See application file for complete search history.

(56) References Cited

PUBLICATIONS

Evans et al., Bacterial Probiotics Induce an Immune Response in the Honey Bee (Hymenoptera: Apidae), Journal of Economic Entomology, 97(3) 752-756 (2004).*
Cherif et al., Versatility of Bacillus thuringiensis in biocontrol: perspectives and limitations of current application, Entomological Research, 37, Suppl 1 (2007) A34-A35.*
Mohr et al., Field study results on the probability and risk of a horizontal gene transfer from transgenic herbicide-resistant oilseed rape pollen to gut bacteria of bees, Appl microbial Biotechnol (2007) 75:573-582.*
Alippi, et al., "Inhibition of the growth of Paenibacillus larvae, the causal agent of American foulbrood of honeybees, by selected strains of aerobic spore-forming bacteria isolated from apiarian sources", Journal of Invertebrate Pathology, vol. 91, No. 3, pp. 141-146 (2006).
Database WPI, Week 201048, Thomson Scientific, JP 2010-H22036 (AN), JP 2010-136668 (PN), Bioproject Co. Ltd. (2010).
Cherif, et al., "Characterization and partial purification of entomocin 110, a newly identified bacteriocin from *Bacillus thuringiensis* subsp. Entomocidus HD110," Microbiological Research, vol. 163, No. 6, pp. 684-692 (2008).
Hansen, et al., "Detection of Enterotoxic Bacillus cereus and Bacillus thuringiensis Strains by PCR Analysis," Applied and Environmental Microbiology, vol. 67, No. 1, pp. 185-189 (2001).

* cited by examiner

*Primary Examiner* — Karen Cochrane Carlson
*Assistant Examiner* — Jennifer M. H. Tichy
(74) *Attorney, Agent, or Firm* — Silvia Salvadori, P.C.; Silvia Salvadori

(57) ABSTRACT

The invention relates to a probiotic mixture of the protection of bees' health, and more specifically for the protection from microbial pathologies, such as those caused by *Paenibacillus larvae*, etiological agent of the American Foulbrood Disease (AFD).

5 Claims, No Drawings

METHODS FOR THE PREVENTION AND CONTROL OF PATHOGENIC INFECTIONS IN BEES AND RELATIVE COMPOSITION

This application is a 371 of PCT/EP2011/057029 filed on 3 May 2011, which claims priority to and the benefit of Italian Application No. MI2010A000776 filed on 4 May 2010, the contents of which are incorporated herein by reference in their entirety.

FIELD OF THE INVENTION

The invention relates to a method for the prevention and the control of pathogenic infections occurring in bees (*Apis mellifera*).

TECHNICAL BACKGROUND

In the last 20 years, the bee-keeping sector registered very consistent losses worldwide, in terms of bee numbers and productivity. These facts had also a negative impact on a broader scale in the agro-alimentary sector. Several factors concurred to this disaster that, only in 2007, led to a loss of 30-50% of the whole Italian and European apiarian patrimony, and of peaks of 60-70% in some areas of the USA. The damage is not limited to the insects' death or the loss of biodiversity. The whole agro-alimentary sector suffers of this problem due to insufficient pollination that can negatively impact the seasonal harvest. Economically, this corresponds to a loss of about a 1 billion € /year distributed as follows: 20 million in USA, 70 million in China, 500 million in Europe, 400 million in the rest of the world. In Italy, only in 2007, 200 thousand beehives were destroyed leading to an economic loss related to missed-pollination of about 250 million euro (equivalent to 1240 euro/beehive) (from press release of APAT—Agency for the environmental protection and technical services—29 Jan. 2008). Among the possible reasons that induce this high mortality are the hygienic conditions of the beehives, the climate change, the availability and quality of feeding and water, electromagnetic pollution and contamination with phyto-pharmaceutical products (neonicotinoids). These stress factors can contribute to decrease the immune defences of the bees thus making them weaker against microbial and viral infections.

The control of microbial and viral diseases is a serious problem because nowadays there are no specific approved medicaments for this purpose. The only solution is the prevention, e.g. preventing the viral or bacterial load from reaching such a level as to induce infections. This can be attained by the adoption of the so-called Good Apiary Practice, avoiding the exchange of materials, sterilizing the instruments and maintaining good ventilation in the beehives. However, this Good Practice may not be enough and the number of epidemic events is constantly increasing. Among them the American Foulbrood Disease (AFD)—the most dangerous disease for the bees' larvae (*Apis mellifera*)—is of great concern because there is not yet a solution [Genersch E., 2009. American Foulbrood in honeybees and its causative agent, *Paenibacillus larvae*. J Invertebr Pathol. 103 Suppl 1:S10-9]. The etiological agent of the AFD is a spore-forming bacterium, *Paenibacillus larvae* [Genersch et al., 2006. Reclassification of *Paenibacillus larvae* subsp. *pulvifaciens* and *Paenibacillus larvae* subsp *larvae* as *Paenibacillus larvae* without subspecies differentiation. Int J Syst Evol Microbiol 56:501-511]. Four subgroups—each one with specific phenotypic characteristics—belong to the species *P. larvae*: ERIC I; ERIC II; ERIC III; ERIC IV [Raugh et al., 2009. Negative correlation between individual-insect level virulence and colony-level virulence of *Paenibacillus larvae*, the etiological agent of American foulbrood of honeybees. Appl Environ Microbiol 75:3344-3347]. ERIC I and ERIC II are the most diffused. This microorganism preferentially infects the young larvae. It is transmitted with the feeding by the adults that nevertheless remain healthy. The use of antibiotics to control the AFD diffusion in Europe is forbidden due to the possible development of antibiotic-resistant pathogens and for reasons of food safety [Miyagi T., Peng C. Y. S., Chuang R. Y., Mussen E. C., Spivak M. S., Doi R. H., 2000. Verification of oxytetracycline-resistant American foulbrood pathogen *Paenibacillus larvae* in the United States. Journal of Invertebrate Pathology 75:95-96]. At the same time, the notification to the authorities of the presence of the AFD in any of the beehives is compulsory, according to the Italian law. Moreover, in accordance with the rules of the Veterinary Police (D.P.R. 8/2/54, n. 320, art. 154-158)—due to the absence of any specific treatment—the only accepted solution is the destruction of the contaminated beehives. The aim of this drastic approach is to avoid the presence of any possible recurrent infection focuses.

As already stated above, in the greatest number of cases, the use of the Good Apiary Practice is not sufficient to avoid the presence of infection focuses.

STATE OF THE ART

The only product available on the market that is proposed as a possible mean to prevent microbial pathologies in bees is ApiGo (Chemicals LAIF). This is a feed supplement for bees, prepared with maltodextrin, yeast extract and vitamins. It is proposed as a prebiotic to re-equilibrate the gastrointestinal microbiota in adult bees and larvae. However, a research conducted on the beekeepers of three Italian regions (i.e. Piemonte, Lombardia and Emilia Romagna) showed that this feed supplement is not effective enough in limiting the diffusion of microbial pathologies in beehives.

The R&D is now focused on the identification of environmental friendly solutions aimed at the bees' protection, the healthiness of the apiary product and the safety of the end-users (consumers).

US2009/0104288. A1 discloses the use of a hop extract to limit the pathogens diffusion in bees.

US2002/0034529A1 discloses the use of a strain of *Paenibacillus larvae pulvifacens* as antagonist of *Paenibacillus larvae larvae*. However, *P. larvae pulvifacens* is a pathogen even if less virulent.

Evans and Lopez [Evans J. D., Lopez D. L., 2004. Bacterial probiotics induce an immune response in the honey bee (Hymenoptera: Apidae). J. Econ. Entomol. 97:752-756.] showed that a mix of probiotics designed for human consumption can increase the production in the bees of two peptides with antimicrobial activity (abaecin and defensin). At the end of the work it is suggested the use of these bacteria as probiotic for bees.

Evans and Armstrong identified at least four microorganisms (*Stenotrophomonas maltophilia*, *Acinetobacter* sp., *Brevibacillus formosus* and *Bacillus fusiformis*)—by means of a metagenomic approach—that can inhibit the growth of *P. larvae* in vitro. The inhibiting action is related to the production of bacteriocines [Evans J. D., Armstrong T. N., 2006. Antagonistic interactions between honey bee bacterial symbionts and implications for disease. BMC Ecol. 6, 4]. Yoshiyama and Kimura have provided same evidences related to the bacteriocines production for other strains

[Yoshiyama M., Kimura K., 2009. Bacteria in the gut of Japanese honeybee, *Apis cerana japonica*, and their antagonistic effect against *Paenibacillus larvae*, the causal agent of American foulbrood. J. Invertebr. Pathol. 102:91-96].

Forsgren et al. [Forsgren E., Olofsson T. C., Vá squez A., Fries I., 2010. Novel lactic acid bacteria inhibiting *Paenibacillus larvae* in honey bee larvae. Apidologie 41:99-108] proposed the use of acetic lactic bacteria isolated from the bees' gut to counteract the infection of *P. larvae*. He showed the efficacy of this approach both in vitro and in vivo. Two possible mechanism of action are proposed: i) the pH decrease due to the production of organic acids; ii) the production of bacteriocines. The use of bacteria (i.e. *Bacillus subtilis*) isolated from the internal organs of bees and from the honey was also proposed by Sabaté et al. [Sabaté D. C., Carrillo L., Audisio M. C., 2009. Inhibition of *Paenibacillus larvae* and *Ascophaera apis* by *Bacillus subtilis* isolated from honeybee gut and honey samples. Res. Microbiol. 160:193-199] to control *Paenibacillus larvae* and *Ascosphaera apis*.

Finally, Alippi e Reynaldi [Alippi A. M., Reynaldi F. J., 2006. Inhibition of the growth of *Paenibacillus larvae*, the causal agent of American foulbrood of honeybees, by selected strains of aerobic spore-forming bacteria isolated from apiarian sources. J. Invertebr. Pathol. 91:141-146] studied the capacity of some isolates to inhibit *P. larvae*. The 10 most interesting strains have been further investigated at biochemical level to identify those factors potentially involved in the inhibition of *P. larvae*.

DESCRIPTION OF THE INVENTION

It has now been found that some microorganisms symbionts of the bees can have a probiotic effect—both on adults and larvae—and can have an immuno-stimulating effect. As a consequence, they are of specific interest for the prevention and control of pathogen infections.

More specifically, the invention relates to a mixture of strains with probiotic activity and capable of preventing bacterial infections induced by *Paenibacillus larvae*, the AFD etiological agent, and by *Melissococcus pluton* (European Foulbrood Disease).

The invention comprises the use of one or more spore-forming bacteria (i.e. *Bacillus thuringensis* and *Brevibacillus laterosporus*), possibly but not necessarily, in association with one or more lactic acid bacteria, such as *Saccharibacter* sp., isolated from *Apis mellifera* or other pollinator. The use of the three microbial species above mentioned is conceived to exert a prebiotic effect in terms of strengthening of the immune system, thus leading to the prevention of the infection of some bee pathogens.

The method of the invention includes the preventive treatment of bees, larvae, beehives and all the other components with the mixture of the invention.

Specific experiments conducted to observe the effect of the probiotic mixture against *Paenibacillus larvae* showed that the mixture had elevated potential in protecting adults and larvae of *Apis mellifera*, by means of a multiple mechanism of action. The treatment led to a higher protection against external stresses and to a substantial improvement in the bees' general health.

Comparative experiments, in which the larvae of *A. mellifera* where exposed to *Paenibacillus larvae* with and without a pre-treatment with the microbial strains of the invention, showed that the mixture is more efficient in preventing the infection as compared to the single strains alone.

It has been shown that the microbial mixture specific of the invention is able to exert a direct antagonist action against the pathogen and at the same time is able to stimulate the immune system of the bee. This stimulation occurs at a wide range with several synergistic mechanisms. This reduces the possibility of development of resistance towards the action of the invention. This is a great advantage because the development of resistant strains is one of the main problems in those countries where the use of antibiotics is still allowed [Lodesani M., Costa C., 2005. Limits of chemotherapy in beekeeping: development of resistance and the problem of residues, Bee World 86:102-109]. Besides, the wide spectrum of action could result to be effective also against other viral or microbial diseases.

More specifically, the in vivo studies on *Apis mellifera* showed that the mixture of bacteria aspecific of the invention is able to:

- modify the pH in the gastrointestinal tract, thus creating an unfavourable environment for the pathogens;
- colonize the gastrointestinal tract of the bee inducing a mechanism of competitive exclusion against the pathogens;
- activate at the same time three mechanisms of regulation of the immune system of the bee: i) production of antimicrobial peptides (AMP), ii) production of the enzyme phenol oxidase involved in the regulation of the process of melanisation, iii) production of lysozyme;
- produce bacteriocines antagonistic for the AFD pathogen.

To summarize, the probiotic mixture specific of the invention is a biological and thus environmental friendly solution to the problem of the bee collapsing disease in that it makes use of bacteria that are symbionts of the bees and that have been isolated from the insect itself.

Biomass Preparation

The dry biomass is prepared by means of a fermentation process of the single strains followed by the lyophilisation of the bacterial biomass.

Dosages and Means of Distribution of the Bacterial Mixture

Examples of formulations and relative means of distribution of the bacterial mixture of the invention are (but are not limited to):

1. Vaporization or spraying of the powder of bacterial biomass previously diluted in plain water. This formulation can be distributed directly on the adult bees, the larvae and any apiarian instrument that can get in contact with the insects. The advised dosage is 200 mL of bacterial suspension per beehive at a final concentration ranging from $1 \times 10^3$ and $1 \times 10^9$ cfu/mL and more specifically from $1 \times 10^5$ and $1 \times 10^7$.
2. Administration of the dry biomass within the syrup. The syrup is a sugar-based product that normally is distributed in the feeding pocket of each beehive. The advised dosage is 700 mL of bacterial suspension per beehive at a final concentration ranging from $1 \times 10^3$ and $1 \times 10^9$ cfu/mL and more specifically from $1 \times 10^5$ and $1 \times 10^7$.
3. Administration by means of solid bar or cake. The bacterial biomass is dissolved in a sugar-based liquid that is then hardened and introduced in the beehive below the top cover. The advised dosage is 500 mL of bacterial suspension per beehive at a final concentration ranging from $1 \times 10^3$ and $1 \times 10^9$ cfu/mL and more specifically from $1 \times 10^5$ and $1 \times 10^7$.

Experimental Section

The effect of the microbial mixture specific of the invention against the pathogens and on the bees' health has been investigated both with in vitro and in vivo studies. The main phases of the investigation have been conducted as follows.

1. Isolation of Strains of *Paenibacillus larvae larvae* from Larvae of *Apis mellifera* Showing the Symptoms of the American Foulbrood Disease Ten larvae have been sampled from a Tunisian and an Italian beehive showing the symptoms of the AFD. The isolation of *Paenibacillus larvae larvae* have been conducted on a medium containing Columbia blood agar as shown in literature [Genersch et al. 2006. Reclassification of *Paenibacillus larvae* subsp *pulvifaciens* and *Paenibacillus larvae* subsp *larvae* as *Paenibacillus larvae* without subspecies differentiation. Int J Syst Evol Microbiol 56:501-511; Bakonyi et al., 2003. Development and evaluation of PCR assays for the detection of *Paenibacillus larvae* in honey samples: comparison with isolation and biochemical characterization. Appl Environ Microbiol 69:1504-1510.]. The molecular typing of the 301 isolates of *Paenibacillus* spp. has been conducted by means of the 16S rRNA gene sequencing and of the amplification genomic repeated sequences (rep-PCR) with primers ERIC. The 16S rRNA sequences have been aligned with the data available in international databases while the ERIC profiles have been compared with those available in literature. Two of the 301 isolates have been identified as ERIC I and ERIC II. These are the most diffused strains of *Paenibacillus* and for this reason these two isolates have been used for all the other experiments.

2. Isolation of Symbiont Bacteria from Larvae and Adults of *Apis mellifera* from Healthy Beehives An Italian beehive with no symptoms of AFD has been chosen as environmental source to isolate bacteria with potential probiotic activity. All the 270 isolates has been identified by means of the 16S rRNA gene sequencing and, in a second phase, the isolates have been grouped in accordance to their metabolic capabilities. Two main groups have been identified: i) 196 acetic bacteria; ii) 64 spore-forming bacteria.

3. In Vitro Screening of the Antagonistic Activity Against *Paenibacillus larvae larvae*

Spore-Forming Bacteria

The 64 spore-forming bacteria have been tested in vitro, by means of an inhibition assay, to investigate the antagonistic activity against the two strains of *Paenibacillus larvae larvae* ERIC I and ERIC II previously selected. The test has been conducted on Tryptic Soy Agar (TSA) as described in Sabaté et al., 2009. [Sabaté D. C., Carrillo L., Audisio M. C., 2009. Inhibition of *Paenibacillus larvae* and Ascophaera apis by *Bacillus subtilis* isolated from honeybee gut and honey samples. Res. Microbiol. 160:193-199].

After 48 h of incubation at 37° C. the antagonistic activity has been evaluated measuring the halo of inhibition of *P. larvae larvae* growth around the tested strains. According to the results of this test, two strains that gave the wider halo (i.e. *Bacillus thuringensis* and *Brevibacillus laterosporus*) were selected for further experiments.

The efficacy of the antagonistic action of the selected bacteria has been evaluated for different concentrations of the *Paenibacillus larvae* larvae strain ERIC I and ERIC II (Table 1). A strain of *Escherichia coli* has been used as negative control.

TABLE 1

Diameter (in cm) of the inhibition halo of the *P. larvae larvae* growth due to the presence of the selected spore-forming symbionts

| Pathogen | *P. larvae larvae* (it) ERIC I | | | *P. larvae larvae* (tn) ERIC II | | |
|---|---|---|---|---|---|---|
| | 20 µl* | 50 µl* | 100 µl* | 20 µl* | 50 µl* | 100 µl* |
| B. thuringensis | 0 | 0 | 0 | 2.8 | 2.1 | BI |
| | 0 | 0 | 0 | ND | 2.2 | BI |
| | 0 | 0 | 0 | ND | 2.3 | BI |
| | 0 | 0 | 0 | ND | 2.2 | BI |
| B. laterosporus | 2 | 3.2 | BI | 1.9 | 1.5 | 1.3 |
| | 1.9 | 2.0 | BI | 1.9 | 1.5 | 1.8 |
| | ND | 2.0 | BI | 1.8 | 1.5 | 1.3 |
| | ND | 2.5 | BI | 1.8 | 1.8 | 1.7 |
| E. coli | 0 | 0 | 0 | 0 | 0 | 0 |
| | 0 | 0 | 0 | 0 | 0 | 0 |
| | 0 | 0 | 0 | 0 | 0 | 0 |
| | 0 | 0 | 0 | 0 | 0 | 0 |

ND = not detected;
BI = blurry inhibition;
*= at a concentration of $10^6$/ml CFU/mL The mechanism of action at the base of the antagonistic activity of the spore-forming bacteria is the production of bacteriocines.

Acetic Acid Bacteria

With the aim of creating a synergistic mixture of bacteria active against *P. larvae larvae*, the metabolic activity of the 196 acetic acid bacteria isolated from *A. mellifera* has been investigated. More precisely, it has been studied how the change of pH induced by the production of lactic acid could play a role in inhibiting the growth of the pathogen without affecting that of *Bacillus thuringensis* and *Brevibacillus laterosporus*.

In Table 2, it is reported the range of pH at which the strains of *P. larvae larvae* ERIC I and ERIC II, *Bacillus thuringensis* and *Brevibacillus laterosporus* could grow.

TABLE 2

Growth assays for *P. larvae larvae, Bacillus thuringensis* and *Brevibacillus laterosporus* in response to a different pH range.

| | pH range | | | | | | | | | | | | | | | | |
|---|---|---|---|---|---|---|---|---|---|---|---|---|---|---|---|---|---|
| | 1 | 1.5 | 2 | 2.5 | 3 | 3.5 | 4 | 4.5 | 5 | 5.5 | 6 | 6.5 | 7 | 7.5 | 8 | 8.5 | 9 |
| P. larvae larvae ERIC I | − | − | − | − | − | − | − | − | − | + | + | + | + | + | + | + | + |
| P. larvae larvae ERIC II | − | − | − | − | − | − | − | − | − | + | + | + | + | + | + | + | + |
| Bacillus | − | − | − | − | − | − | − | + | + | + | + | + | + | ND | ND | ND | ND |

TABLE 2-continued

Growth assays for *P. larvae larvae*, *Bacillus thuringensis* and *Brevibacillus laterosporus* in response to a different pH range.

| | pH range | | | | | | | | | | | | | | | | |
|---|---|---|---|---|---|---|---|---|---|---|---|---|---|---|---|---|---|
| | 1 | 1.5 | 2 | 2.5 | 3 | 3.5 | 4 | 4.5 | 5 | 5.5 | 6 | 6.5 | 7 | 7.5 | 8 | 8.5 | 9 |
| *Thuringensis Brevibacillus Laterosporus* | − | − | − | − | − | − | − | + | + | + | + | + | + | ND | ND | ND | ND |

ND = non determined;
\+ = positive growth;
− = no growth

TABLE 3

Results of the in vivo experiments to assess the degree of protection from *P. larvae larvae* of *A. mellifera* when treated with the probiotic strains *Bacillus thuringensis*, *Brevibacillus laterosporus*, *Saccharibacter* sp. an a non-probiotic *E. coli*. Significant differences between the treatments were evaluated by means of one way ANOVA, and individual means were compared using the Tukey's test. Samples with different letters are statistically different ($p > 0.05$).

| Treatment | Mortality of *Apis mellifera* larvae when exposed to *P. larvae larvae* | ANOVA |
|---|---|---|
| Diet (basal mortality) | 23% | a |
| Diet + *P. larvae larvae* | 70% | b |
| Diet + *P. larvae larvae* + *E. coli* | 40% | c |
| Diet + *Saccharibacter* sp. + *P. larvae larvae* | 25% | a |
| Diet + *Bac. thuringensis* + *P. larvae larvae* | 24% | a |
| Diet + *Bre. laterosporus* + *P. larvae larvae* | 24% | a |
| Diet + Mix of the 2 spore-forming strains + *P. larvae larvae* | 22% | a |

The growth of the pathogenic strains of *P. larvae larvae* was inhibited at pH values lower than 5.5, while the probiotic strains *Bacillus thuringensis* and *Brevibacillus laterosporus* could grow at a pH of a unit lower (4.5), indicating a higher tolerance to sub-acidic environments as compared to the pathogen. Subsequently, considering that a pH range of 4.5-5.5 could support the growth of *Bacillus thuringensis* and *Brevibacillus laterosporus* but not of *P. larvae larvae* ERIC I and ERIC II, we identified which of the lactic acid bacteria was able to decrease the pH of the growth medium to values below 5.5. A strain of *Saccharibacter* sp., isolated from healthy bees resulted to be the best candidate also in reason of the fact that it could easily grow in co-culture with *Bacillus thuringensis* and *Brevibacillus laterosporus*.

The widespread association of *Saccharibacter* sp. and/or other acetic acid bacteria with larvae and adults of healthy bees has been shown by means of PCR-DGGE (Denaturing Gradient Gel Electrophoresis), a culture independent molecular fingerprinting technique.

4. In Vivo Antagonistic Activity of the Selected Bacteria Against *Paenibacillus larvae larvae*. Effect of the Single Strains and the Mixture Thereof.

The in vivo studies proved the efficacy of the mixture in improving and protecting the *Apis mellifera*'s health. The efficacy of the invention was tested on 2046 *Apis mellifera* larvae of different age (between 12 and 36 hours, the period of highest susceptibility for the infection) from 10 different beehives. The experiments (conducted in batches of approximately 500 larvae each) showed that the addition of the bacterial mix to the diet was able to protect the larvae from AFD infection. The larvae's mortality ranged between 50% and 90% in presence of *Paenibacillus larvae*. The mortality level decreased to values similar to that of the larvae non-exposed to the pathogen when previously treated with the strains of the invention. A 90% to 100% survival, as compared to the control, was reached both with the single strains and with the mixture of bacteria, with the latter providing the best effect.

The in vivo results are summarized in Table 3.

The isolated probiotic strains have been also tested for their capacity in colonizing the bee's gastrointestinal tract, thus inducing a mechanism of competitive exclusion against the pathogen. Adults of *A. mellifera* have been fed with a sugar diet supplemented with the probiotic strains for three days. Subsequently the probiotic strains in the diet have been substituted with the pathogen. After a week, the gut content have been plated on selective medium to investigate for the presence of the pathogen. It was not possible to retrieve the presence of the pathogen while *Bacillus thuringensis, Brevibacillus laterosporus* and *Saccharibacter* sp. have been re-isolated and characterized by means of molecular techniques. This approach showed that the bacteria of the invention became dominant within the gut-associated microbial community.

5. Immune Stimulating Activity of the Selected Probiotic Mixture in Larvae and Adults of *Apis mellifera*

The immune system of the invertebrates controls the infections by means of two mechanisms: i) the humoral response mediated by soluble peptides with antimicrobial activity (AMP), proteases, etc. . . . ; ii) the cellular response. Typical AMP involved in the first mechanism are the defensins or abaecin, substances that can induce the lysis of microorganisms. Another example of humoral response is the production of lysozyme, production that is regulated by three genes (lys1-3). The cellular response includes the phagocytosis of the hemocytes, the encapsulation and the nodulation. More specifically, in the process of encapsulation, the pathogen is surrounded by a layer mainly composed of melanin (melanisation). This layer adheres to the pathogen tissues and forms a barrier that isolates the invader. The process of melanisation is mediated by the enzyme phenoloxidase and is regulated by the gene proPOact.

In order to investigate whether the probiotic strains of the invention were able to stimulate the main mechanisms of the *Apis mellifera*'s immune system we investigated the levels of transcription of the genes i) coding for abaecin; ii) defensin I iii) lys-1 iv) proPOact, and v) hym (hymenoptaecin) in ten larvae and ten adults fed with a diet amended with a the mixture of bacteria of the invention (20 μl of *Bacillus thuringensis* and *Brevibacillus laterosporus* at a final concentration of $3\times10^4$ cellule/μl) as compared to five larvae fed with the basal diet (fructose, glucose, yeast extract and royal jelly). After three days of treatment and one day of fasting, the total RNA has been extracted from each larvae/adult. The genes expression has been quantified by means of Real-Time qPCR with specific primers. The treatment with the mixture of probiotic bacteria was able to induce a statistically significant increase (ratio with the insect 5S) of the genes defensin I (+0.5 Log) and Hym (+2.8 Log) in the larvae and of all the investigated genes in the adults: abaecin (+0.1 Log) defensin I (+3.8 Log) lys-1 (+0.5 Log) proPOact (+0.1 Log) and Hym (+2.8 Log). In the control situation (basal sugar diet) no significant changes in the expression of the investigated genes was observed.

The invention claimed is:

1. Method for control and prevention of bacterial diseases of bees, comprising contacting bees/larvae, honeycombs or hives with an effective quantity of a lyophilized composition comprising two spore-forming bacteria selected from *Bacillus thuringensis* and *Brevibacillus laterosporus*, wherein contacting causes pH to decrease to below 5.5 in a gut of the bees.

2. Method as claimed in claim 1, wherein the bacterial bee disease is caused by *Paenibacillus larvae* or *Melissococcus pluton*.

3. Method as claimed in claim 1, wherein the composition is in the form of a dry bacterial biomass in powder form for dilution in water, syrup, sugar syrup, solid bar or cake.

4. Method as claimed in claim 1, wherein the two spore-forming bacteria are combined with an acetic acid bacterium.

5. Method as claimed in claim 4, wherein the acetic acid bacterium is *Saccharibacter* sp.

* * * * *